United States Patent
Kiene et al.

(10) Patent No.: US 6,899,228 B2
(45) Date of Patent: May 31, 2005

(54) PANEL FOR RECEIVING CASSETTES AND/OR SPECIMEN SLIDES FOR HISTOLOGICAL OR CYTOLOGICAL PREPARATIONS

(75) Inventors: Uwe Kiene, Eppelheim (DE); Manfred Biehl, Meckesheim (DE); Holger Metzner, Nussloch (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 10/442,992

(22) Filed: May 21, 2003

(65) Prior Publication Data

US 2003/0217945 A1 Nov. 27, 2003

(30) Foreign Application Priority Data

May 25, 2002 (DE) .......................................... 102 23 412

(51) Int. Cl.⁷ .............................................. B65D 85/48
(52) U.S. Cl. ..................................... 206/456; 220/345.1
(58) Field of Search ................................. 206/454, 455, 206/456, 449, 425, 509, 511, 512; 220/345.1, 345.2, 345.3

(56) References Cited

U.S. PATENT DOCUMENTS

| | | | | |
|---|---|---|---|---|
| 2,858,016 A | * | 10/1958 | Marano | 206/425 |
| 4,139,097 A | * | 2/1979 | Bowman et al. | 206/425 |
| 4,520,928 A | * | 6/1985 | Wilson | 206/505 |
| 4,643,306 A | * | 2/1987 | Ryan | 206/425 |
| 5,609,252 A | * | 3/1997 | Koch | 206/455 |
| 5,938,031 A | * | 8/1999 | Woods | 206/455 |
| 6,427,836 B1 | * | 8/2002 | Bolanos | 206/449 |
| 6,446,807 B1 | | 9/2002 | Lafond et al. | |

FOREIGN PATENT DOCUMENTS

DE    101 15 065 A 1    10/2002

* cited by examiner

*Primary Examiner*—Shian T. Luong
(74) *Attorney, Agent, or Firm*—Hodgson Russ LLP

(57) ABSTRACT

A panel (1) for receiving cassettes (2) and/or specimen slides (3) for histological or cytological preparations is embodied in rectangular fashion with two longitudinal sides (4), a first narrow side (5) and a second narrow side (6), and comprises a base (7) as support for the specimen slides (3) and/or cassettes (2). Peripheral side walls (8) are provided on both longitudinal sides (4) and on the first narrow side (5).

8 Claims, 2 Drawing Sheets

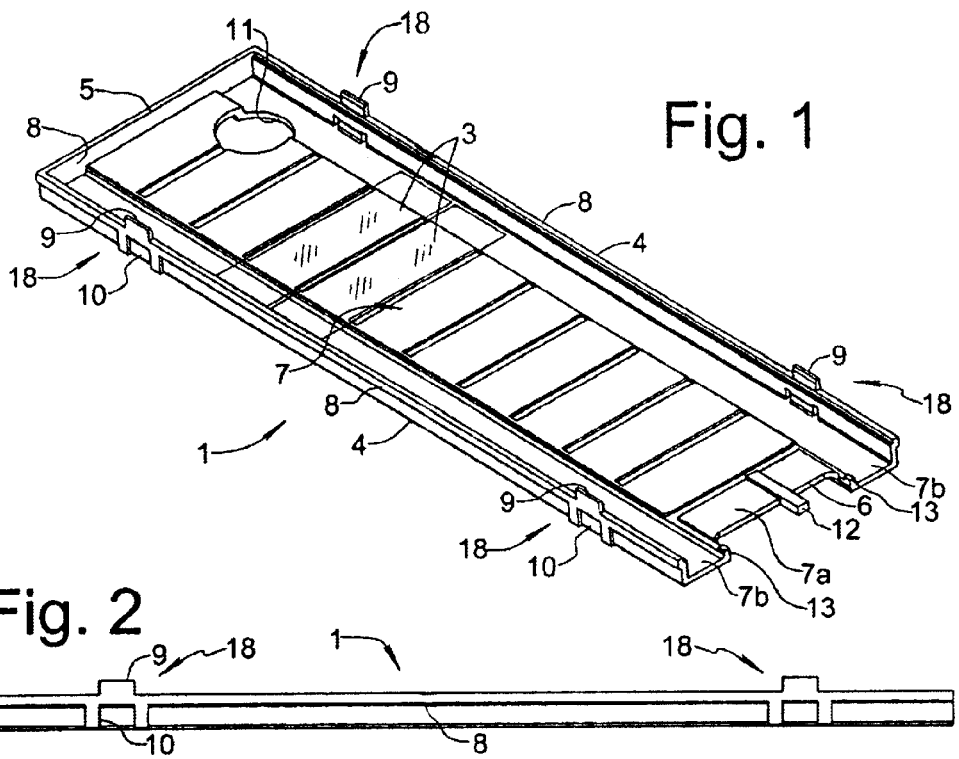
Fig. 1
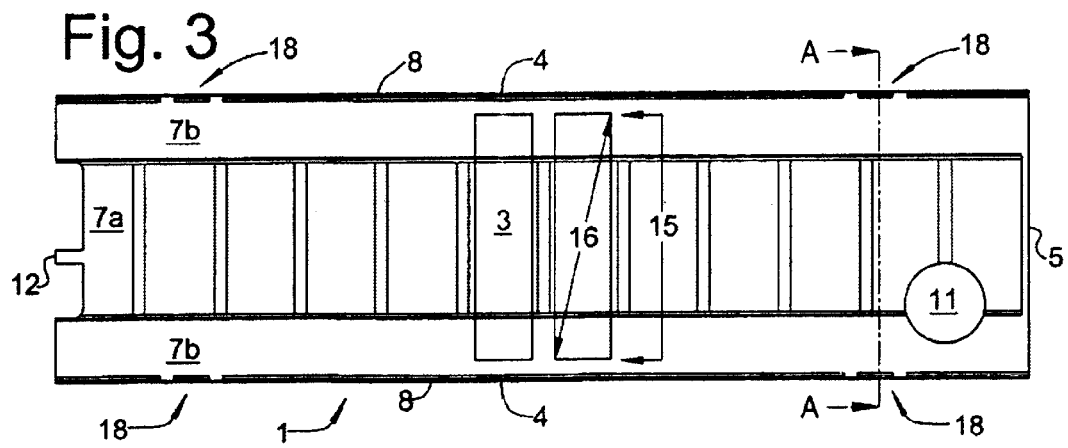
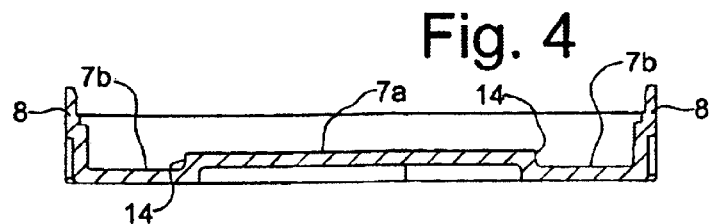

PANEL FOR RECEIVING CASSETTES AND/OR SPECIMEN SLIDES FOR HISTOLOGICAL OR CYTOLOGICAL PREPARATIONS

CROSS REFERENCE TO RELATED APPLICATIONS

This application claims priority of the German patent application 102 23 412.4 filed May 25, 2002 which is incorporated by reference herein.

FIELD OF THE INVENTION

The invention concerns a panel for receiving cassettes and/or specimen slides for histological or cytological preparations.

BACKGROUND OF THE INVENTION

Unpublished German Patent Application DE 101 15 065.2 discloses an apparatus for imprinting cassettes and/or specimen slides for histological or cytological preparations in a printing system. This printing system is characterized in that the cassettes and/or specimen slides are imprinted in computer-controlled fashion by an inkjet printer, and this applied ink is then dried by way of a flash device. The flash device is followed by a removal device for depositing the imprinted cassettes and/or imprinted specimen slides.

This removal device can be equipped with an apparatus for collecting the cassettes and/or specimen slides. A collection apparatus of this kind is described in the unpublished German Patent Application entitled "Apparatus for collecting cassettes and/or specimen slides for histological or cytological preparations." In this Application, panels are used to collect the imprinted cassettes and/or specimen slides and remove them from the printing system.

The cassettes and/or specimen slides collected on the panels are then transported on the panels for further processing in the laboratory.

SUMMARY OF THE INVENTION

It is therefore the object of the present invention to configure the panels so that utilization in a collection apparatus of this kind is possible, and secure transport of the collected cassettes and/or specimen slides is simultaneously possible.

The invention is characterized in that the panel is embodied in rectangular fashion with two longitudinal sides, two narrow sides, and a base. The base forms the support for the specimen slides and/or cassettes. Peripheral side walls are provided on both longitudinal sides and on one narrow side. The other narrow side is open, so that the specimen slides and/or cassettes can be slid onto the panel from that side.

In a development of the invention, the side walls of the longitudinal sides are equipped with shaped-on (integrally formed with the side wall) lugs. The panel also comprises grooves into which these shaped-on lugs fit, so that multiple panels are configured, by way of these grooves and lugs, to be stackable. Provision is made both for panels that receive cassettes and specimen slides, and for panels that receive only cassettes or only specimen slides, to be stackable by way of the connection.

In a further embodiment of the invention, the base of the panel has a circular opening whose purpose is that an external sensor can detect the fill level of the panel through the opening.

In a development of the invention, the panel has on its open narrow side a triggering tab that can engage into a photoelectric barrier, and the position of the panel is thereby detected.

As a particular development, the triggering tab is arranged beneath the base on the panel so that a transfer position for the specimen slides and/or cassettes onto the panel can be set by way of the arrangement of a photoelectric barrier.

In a development of the invention, two stops are provided on the second or open narrow side of the panel, preventing specimen slides and/or cassettes from falling out during transport in the laboratory.

In a further embodiment of the invention, the base of the panel is provided with a step so that the base is subdivided into a higher and a lower part. This is advantageous in particular for cassettes having shaped-on covers, so that the lower base then forms the support for the cassette, and the higher base the support for the cover of the cassette. The height of the step can be approx. 6 mm.

If the step is arranged on a side wall of the panel, the thin specimen slides can be removed more easily from the panels. All that is necessary is to push on the specimen slide in the region of the lower base, so that the specimen slide lifts up from the higher base support and can then be removed. In this case it is entirely sufficient if the step is approx. 1–3 mm.

In a particular embodiment of the invention, the panel is embodied as a one-piece injection-molded plastic part. The panel can be dimensioned in such a way that the longitudinal extension is no greater than 35 cm, and the extension on the narrow side is no more than 10 cm.

In an embodiment of the invention, the panels are used in an apparatus for collecting cassettes and/or specimen slides, in which context the collection apparatus can be a constituent of a printing device.

In a particular embodiment of the invention, the lengths of the two narrow sides are dimensioned to be greater than the longitudinal extension of the specimen slide and/or cassette, and simultaneously the length of the two narrow sides is dimensioned to be less than the diagonal of the longitudinal extension of the specimen slide and/or cassette. The result, in particularly advantageous fashion, is that sufficient clearance is present when the panels are loaded with specimen slides and/or with cassettes; and moreover the specimen slides and/or cassettes are effectively prevented from falling out when the panels are transported. If the panels are tilted during transport, the specimen slides and/or cassettes become jammed, with their respectively diagonally opposite corners, into the side walls of the longitudinal sides of the panel. The result that can be achieved, especially in the case of sharp-edged glass specimen slides, is that specimen slides do not fall out of the panel even when the panel is held vertically.

BRIEF DESCRIPTION OF THE DRAWINGS

The invention will be depicted and explained in more detail using two exemplary embodiments with reference to the schematic drawings, in which:

FIG. 1 is a view of the panel with specimen slides in place;

FIG. 2 is a side view of the panel according to FIG. 1;

FIG. 3 is a plan view of the panel with specimen slides in place;

FIG. 4 is a section through the panel along line A—A of FIG. 3;

DETAILED DESCRIPTION OF THE INVENTION

Figure 5:
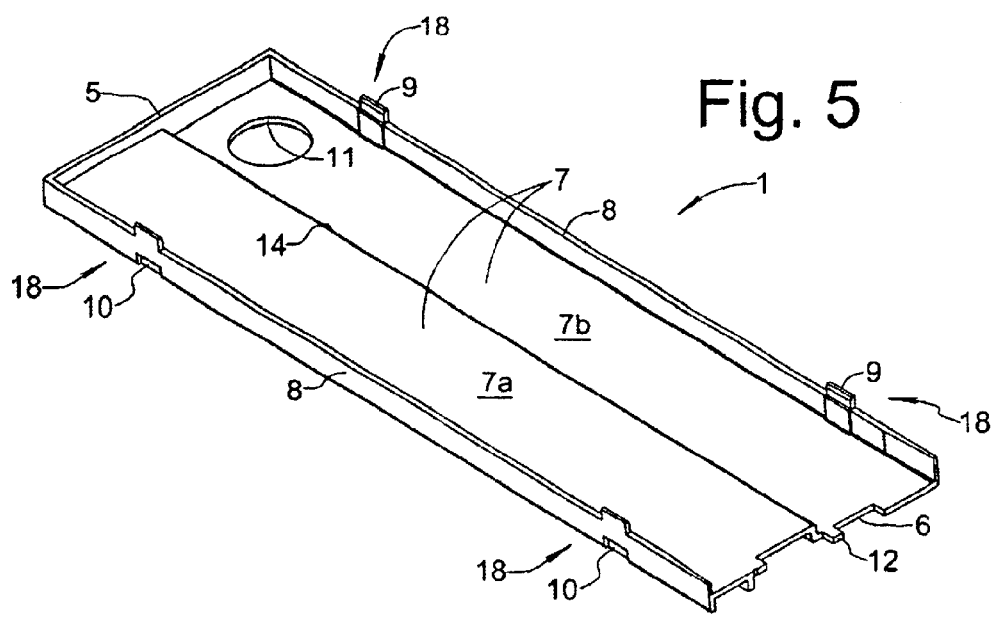
FIG. 5 is a view of the panel for cassettes.

FIG. 1 is a view of panel 1 with specimen slides 3 in place. Panel 1 is of rectangular configuration and has two longitudinal sides 4 as well as a first narrow side 5, a second narrow side 6, and a base 7. A peripheral side wall 8 is provided on the two longitudinal sides 4 and on first narrow side 5. Base 7 is subdivided by steps 14 (FIG. 4) into a higher base part 7a as support for specimen slides 3, and two lower base parts 7b.

Provided on second narrow side 6 of panel 1 is a triggering tab 12, shaped onto higher base part 7a, whose underside lies in one plane with the underside of lower base part 7b and whose upper side lies in one plane with the underside of higher base part 7a.

Higher base part 7a moreover has two stops 13 that prevent the inserted specimen slides from falling out while panel 1 is being transported.

A circular opening 11, through which a sensor can detect a specimen slide 3 or a full panel 1, is provided in base 7 of panel 1.

Four lug and groove members 18 are provided on peripheral side walls 8, two lug and groove members on each of the two peripheral side walls 8. Each lug member 18 includes a lug 9 and a groove 10. By way of lugs 9 and grooves 10, several panels 1 can be stacked one above another.

FIG. 2 is a side view of the panel shown in FIG. 1, with side wall 8 and lugs 9 shaped thereonto and grooves 10 that are provided.

FIG. 3 shows panel 1 with specimen slides 3, which have a longitudinal extension 15 and a diagonal 16, in place. If the length of first narrow side 5 and second narrow side 6 of panel 1 is selected to be less than the length of diagonals 16, the diagonally opposite corners of the specimen slide can jam into place on peripheral side wall 8, so that none of specimen slides 3 can fall out while the panel is being transported.

FIG. 4 is a section through panel 1 along line A—A according to FIG. 3. Higher base part 7a and two lower base parts 7b are formed by means of the two steps 14. Higher base part 7a constitutes the support for the specimen slides, in which context the specimen slide projects with its ends over lower base parts 7b. A single specimen slide can easily be removed by tilting one end of the specimen slide onto the associated lower base part 7b.

Figure 8:
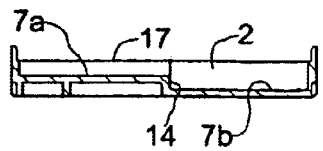
FIG. 8 is a section through the panel along line A—A of FIG. 7, with a cassette in place.

FIG. 5 is a view of panel 1 for cassettes 2 (FIG. 8), base 7 being subdivided here as well, by means of a step 14, into a higher base part 7a and a lower base part 7b. Lower base part 7b serves as support for the cassette, and higher base part 7a as support for cover 17 shaped onto the cassette (FIG. 8).

Triggering tab 12 is in this case shaped on in the plane of lower base part 7b.

Figure 6:
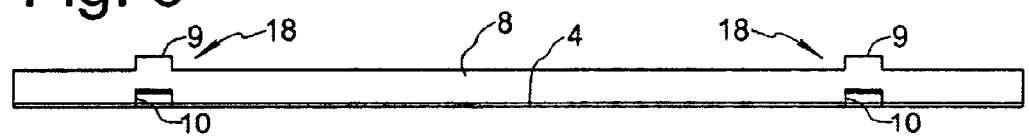
FIG. 6 is a side view of the panel according to FIG. 5.

FIG. 6 is a side view of the panel according to FIG. 5, with side wall 8 and lugs 9 shaped thereonto and grooves 10 that are provided.

Figure 7:
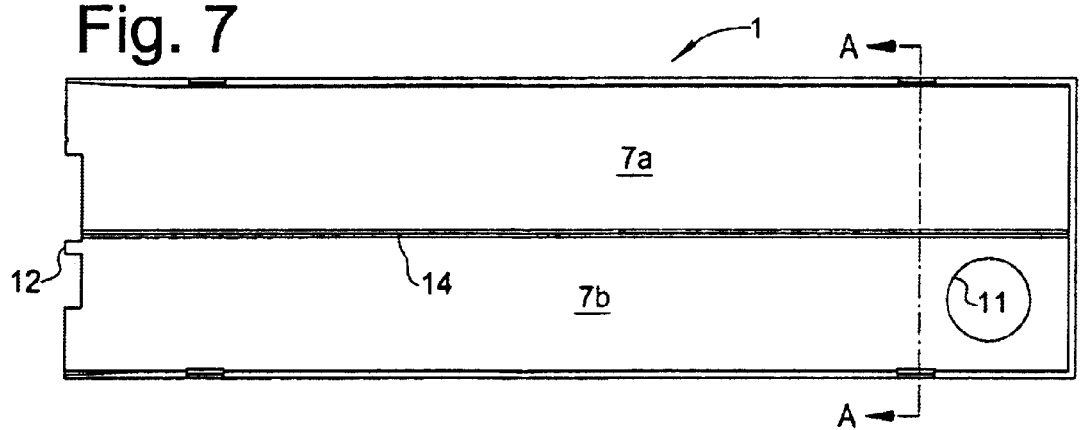
FIG. 7 is a plan view of the panel according to FIG. 5.

FIG. 7 shows panel 1 in a plan view, with the two base parts 7a and 7b separated by step 14.

FIG. 8 is a section through the panel along line A—A according to FIG. 7, with cassette 2 in place and shaped-on cover 17. It is evident from this Figure that cassette 2 rests on lower base part 7b, and cover 17 on higher base part 7a.

The two exemplary embodiments herein depicted and described of the panels for cassettes and specimen slides are specifically optimized therefor. It is, of course, also possible to collect cassettes with and without covers on the panel for specimen slides, and specimen slides on the panel for cassettes.

| PARTS LIST | |
|---|---|
| 1 | Panel |
| 2 | Cassette |
| 3 | Specimen slide |
| 4 | Longitudinal side |
| 5 | First narrow side |
| 6 | Second narrow side |
| 7 | Base |
| 7a | Higher base part |
| 7b | Lower base part |
| 8 | Side wall |
| 9 | Lug |
| 10 | Groove |
| 11 | Opening |
| 12 | Triggering tab |
| 13 | Stop |
| 14 | Step |
| 15 | Longitudinal extension of (3) |
| 16 | Diagonal of (3) |
| 17 | Cover |
| 18 | Lug and groove member |

What is claimed is:

1. A panel (1) for receiving cassettes (2) and/or specimen slides (3) for histological or cytological preparations, each cassette and specimen slide having a longitudinal extent (15) and a diagonal extent (16), the panel comprising:

a pair of longitudinal sides (4), a first narrow side (5), and a second narrow side (6), the pair of longitudinal sides (4) and the first and second narrow sides (5 and 6) forming a rectangular configuration;

a base (7) connecting the pair of longitudinal sides (4) and the first and second narrow sides (5 and 6) to one another, the base (7) supporting received cassettes and/or specimen slides;

a pair of peripheral side walls (8) one along each of the pair of longitudinal sides (4), and a peripheral side wall (8) along the first narrow side (5), wherein the pair of peripheral side walls (8) include a plurality of lug and groove members (18) each defining a lug (9) and a groove (10) adjacent the lug (9); and a triggering tab (12) on the second narrow side (6) of the panel (1);

whereby several of the panels can be stacked one above another by fitting the lugs (9) of one panel into the grooves (10) of another panel.

2. The panel as defined in claim 1, wherein the lug and groove members are integrally formed with an associated side wall (8).

3. The panel (1) as defined in claim 1, wherein the base (7) of the panel (1) includes an opening (11).

4. The panel (1) as defined in claim 1, wherein the triggering tab (12) is arranged beneath the base (7).

5. The panel (1) as defined in claim 1, further comprising a pair of stops (13) are provided on the second narrow side (6) of the panel (1).

6. The panel (1) as defined in claim 1, wherein the base (7) includes at least one step (14) which divides the base (7) into at least one higher base part (7*a*) and at least one lower base part (7*b*).

7. The panel (1) as defined in claim 1, wherein the panel (1) is embodied as a one-piece injection-molded plastic part.

8. The panel (1) as defined in claim 1, wherein the lengths of the two narrow sides (5 and 6) are dimensioned to be greater than the longitudinal extent (15) but less than the diagonal extent (16).

* * * * *